United States Patent [19]
Martinelli et al.

[11] Patent Number: 6,083,689
[45] Date of Patent: Jul. 4, 2000

[54] SENSITIVE IMMUNOASSAYS UTILIZING ANTIBODY CONJUGATES WITH REPLICABLE DNA TEMPLATES

[75] Inventors: Richard A. Martinelli, Brighton; Eddie Carroll, III, Waltham, both of Mass.

[73] Assignee: Bayer Corporation, East Walpole, Mass.

[21] Appl. No.: 08/416,571

[22] Filed: Apr. 4, 1995

Related U.S. Application Data

[63] Continuation-in-part of application No. 08/352,670, Dec. 9, 1994, which is a continuation of application No. 08/015,249, Feb. 5, 1993, Pat. No. 5,407,798, which is a continuation of application No. 07/598,269, Oct. 16, 1990, abandoned.

[51] Int. Cl.$^7$ ............................ C12Q 1/68; G01N 33/53; G01N 33/536; G01N 33/543
[52] U.S. Cl. ............................ 435/6; 435/7.1; 435/7.5; 435/7.72; 435/7.91; 435/7.92; 435/91.24; 435/91.51; 435/971; 435/973; 436/518; 436/536; 436/547; 436/824; 436/828
[58] Field of Search ............................ 435/6, 7.1, 7.5, 435/7.72, 7.91, 7.92, 91.21, 91.51, 971, 973; 436/518, 536, 547, 824, 828

[56] References Cited

U.S. PATENT DOCUMENTS

| | | |
|---|---|---|
| 4,786,600 | 11/1988 | Kramer et al. . |
| 4,883,750 | 11/1989 | Whiteley et al. . |
| 4,957,858 | 9/1990 | Chu et al. . |
| 5,112,734 | 5/1992 | Kramer et al. . |
| 5,242,794 | 9/1993 | Whiteley et al. . |
| 5,395,752 | 3/1995 | Law et al. . |
| 5,407,798 | 4/1995 | Martinelli et al. . |
| 5,451,505 | 9/1995 | Dollinger . |

FOREIGN PATENT DOCUMENTS

| | | |
|---|---|---|
| 481704 | 4/1992 | European Pat. Off. . |
| 9006376 | 6/1990 | WIPO . |
| 9014439 | 11/1990 | WIPO . |

OTHER PUBLICATIONS

Cahill et al., "Polymerase Chain Reaction and Qβ Replicase Amplification," *Clinical Chemistry*, 37(9): 1482–1485 (1991).

Chu et al., "Synthesis of an amplifiable reporter RNA for bioassays," *Nucleic Acids Research*, 14(14): 5591–5603.

Feix and Sano, "Polydeoxribonucleoteids as Templates for RNA Synthesis Catalysed by Qβ Replicase," *FEBS Letters*, 63(1): 201–204 (Mar. 1976).

Kramer and Lizardi, "Replicatable RNA Reporters," *Nature*, 339: 401–402 (Jun. 1, 1989).

Lizardi et al., "Exponential Amplification of Recombinant–RNA Hybridization Probes," *Bio/Technology*, 6: 1197–1202 (Oct. 1988).

Lizardi and Kramer, "Exponential amplification of nucleic acids: new diagnostics using DNA polymerases and RNA replicases," *Tibtech*, 9: 53–58 (Feb. 1991).

Miele et al., "Autocatalytic Replication of a Recombinant RNA," *J. Mol. Biol.*, 171: 281–295 (1993).

Mills et al., "Qβ Replicase: Mapping the functional Domains of an RNA–dependent RNA polymerase," *J. Mol. Biol.*, 205: 751–764 (1988).

Sano et al., "Immuno–PCR: Very Sensitive Antigen Detection by Means of Specific Antibody–DNA Conjugates," *Science*, 258: 120–122 (Oct. 2, 1992).

Zhang, "QBeta Replicase–Directed RNA Polymerization (QBeta Replicase)," *Diss. Abstr. Intl.*, 53/11–B, 5568 (1992) (Ph. D. Thesis/Abstr.).

*Primary Examiner*—Nita Minnifield
*Assistant Examiner*—Khalid Masood
*Attorney, Agent, or Firm*—Leona L. Lauder; Arthur S. Morgenstern

[57] ABSTRACT

A novel signal amplification system for immunoassays that minimizes non-specific signals is disclosed. Immunoassay methods, reagents and test kits are described for obtaining immunoassays of enhanced sensitivity. The reagents include antibody-variant DNA conjugates, wherein the variant DNA is a substrate for an RNA-dependent RNA polymerase, such as, QB replicase. Immunoassay methods to detect, or to detect and quantitate, analyte in test samples comprise transcribing the variant DNA of said antibody-DNA conjugates that are bound to analyte, to RNA, and replicating the RNA transcripts, wherein the presence or quantity of variant RNA replication products can be correlated with the presence or quantity of analyte in the test samples. Further, methods are provided to detect, or to detect and quantitate, simultaneously two or more analytes in a test sample.

18 Claims, No Drawings

SENSITIVE IMMUNOASSAYS UTILIZING ANTIBODY CONJUGATES WITH REPLICABLE DNA TEMPLATES

This application is a continuation-in-part of U.S. Ser. No. 08/352,670 (filed Dec. 9, 1994) which is now pending and is a continuation of U.S. Ser. No. 08/015,249 (filed Feb. 5, 1993), which was issued as U.S. Pat. No. 5,407,798 on Apr. 18, 1995, and which is a continuation of now abandoned U.S. Ser. No. 07/598,269 (filed on Oct. 16, 1990). Priority is claimed from each of those applications and from that patent.

FIELD OF THE INVENTION

This invention is in the general field of immunochemistry. More specifically, the invention concerns sensitive immunoassays wherein antibodies conjugated to variant DNA templates are used with an appropriate RNA-dependent RNA polymerase, such as, QB replicase, in a novel signal amplification system that minimizes unwanted background signal.

BACKGROUND OF THE INVENTION

Immunoassays for specific antigens are powerful tools for clinical diagnostics and for various molecular and cellular analyses. The instant invention is directed at enhancing the sensitivity of immunoassays by employing variant DNA as an amplifiable reporter molecule.

The sensitivity of conventional immunoassays is in practice governed for a particular antibody-analyte interaction by the value of the equilibrium constant, which is normally referred to as the dissociation constant. The equilibrium or dissociation constant reflects the amount of antibody-analyte complex formed at given concentrations of reactants. Typical values for the dissociation constant are found in the range of $10^{-7}$ M to $10^{-12}$ M. For example, at an antibody concentration equal to the dissociation constant, approximately 50% of a trace analyte will be complexed with the antibody at equilibrium.

Efforts to maximize sensitivity for immunoassays have included attaching labels, such as, enzymes, to antibodies such that the number of antibody-analyte complexes which can be detected is maximized. The ultimate goal in such an approach is to be able to detect a single analyte-antibody complex.

An article by Chu et al., [*Nucleic Acids Research*, 14: 5591 (1986)], concerns the use of midivariant RNA as an amplifiable reporter to enhance the sensitivity of bioassays. Midivariant RNA serves as a template for its own replication which is catalyzed by QB replicase. [Miele et al., *J. Mol. Biol.*, 171: 281 (1983).] A single molecule of midivariant RNA theoretically could be amplified by QB replicase to give sufficient copies to enable detection by conventional radioactive and non-radioactive techniques. Chu et al., supra state at page 5602 that "the theoretical sensitivity of an assay system that uses . . . [midivariant RNA as a] replicable reporter should be close to one molecule of target." However Chu et al. go on to state that they "anticipate that the detection limits that can be reached in practice will be determined by irreducible, nonspecific adsorption of the receptor to the sample."

That problem of nonspecific adsorption of a receptor carrying such a midivariant RNA label could be a serious drawback because of the efficiency with which the midivariant RNA template may be replicated. Midivariant RNA templates from a relatively few nonspecifically adsorbed receptors could result in an extremely high background signal which could obscure the signal from specifically bound receptors. The sensitivity of such an assay using midivariant RNA as an amplifiable reporter would be therefor limited.

This invention solves that problem by using variant DNAs, rather than midivariant RNA, as templates for RNA synthesis with appropriate RNA-dependent RNA polymerases, such as, QB replicase. As variant DNA templates, such as, nanovariant and midivariant DNA templates, do not replicate as efficiently as their RNA counterparts, such DNA templates overcome the potential problem of extremely high background signal that could occur if variant RNA templates were used.

The immunoassay methodology of this invention employs variant DNA as an amplifiable label conjugated to an antibody or biologically active antibody fragment. The advantages for the use of the amplifiable DNA templates of this invention over their RNA counterparts as labels for antibodies are several. First, current methods of synthesizing DNA oligonucleotides are further advanced than for their RNA counterparts. Second, DNA is inherently more stable than RNA. Also, as indicated above, the relative inefficiency of the replication of the DNA templates can be used effectively to mask the potential signal generated from non-specific binding of the antibody conjugates, and thus, the assays of this invention should be more sensitive than assays employing corresponding RNA template conjugates.

SUMMARY OF THE INVENTION

This invention in one aspect concerns immunoassay methods that use an antibody-variant DNA conjugate as a tracer antibody, wherein the variant DNA is a substrate for an RNA-dependent RNA polymerase. The use of said conjugate provides a novel signal amplification system for immunoassays.

The antibody of the conjugate can be directed to either an analyte under assay or to an anti-analyte antibody used in an immunoassay. After incubation and separation of unbound antibody-variant DNA conjugate from that bound to the analyte under assay, the variant DNA template, bound to the analyte, is transcribed, and the RNA transcript is replicated by contact with an appropriate amount of an RNA-dependent RNA polymerase, whose substrate is the variant DNA, in the presence of ribonucleotides.

The detection of RNA replication products produced in the assay, indicates the presence of the analyte under assay. The RNA replication products can also be quantitated, and the quantity of the replication products can be correlated with the quantity of the analyte assayed. Thus, the immunoassay methods of this invention can be used for detecting or, for detecting and quantitating analyte in a test sample.

Further, immunoassay methods of this invention can be used to detect, or to detect and quantitate, simultaneously two or more analytes in a test sample. Such methods comprise the use of two or more different antibody-variant DNA conjugates, wherein the variant DNA of different conjugates comprise different inserted DNA sequences inserted therein, and wherein said inserted DNA sequences do not correspond to naturally occurring variant RNA sequences that are templates for RNA-dependent RNA polymerases. Those DNA sequences are preferably non-variant DNA. The inserted DNA sequences are preferably inserted at a position in the variant DNA other than within 10 bases from the 3' end, more preferably other than within 20 bases from the 3' end.

In some embodiments of methods to detect, or to detect and quantitate, simultaneously two or more different analytes in test samples, the antibodies of different conjugates, that is, antibodies conjugated to variant DNA containing different inserted DNA sequences, are specific for different analytes, whereas antibodies that are conjugated to variant DNA containing the same inserted DNA sequence are specific for the same analyte. Nucleic acid probes, preferably RNA probes, that are complementary to the different variant RNA replication products are preferably used to detect, or, to detect and quantitate the RNA replication products of such immunoassay methods. Probes complementary to the same variant RNA replication products are similarly labeled, whereas probes complementary to different variant RNA replication products are differently labeled.

Immunoassay reagents comprising the antibody-variant DNA conjugates of this invention are described below, as well as representative methods of preparing such conjugates. Exemplary immunoassay reagents include those wherein the variant DNA of said antibody-variant DNA conjugates is conjugated to the antibody of said conjugates through an avidin-biotin, preferably streptavidin-biotin, bridge, via Protein A, or by means of a heterobifunctional linking agent. Other exemplary regents can include variant DNA conjugated to avidin and/or Protein A.

Different DNA sequences, as indicated above, can be inserted in the variant DNA of the immunoassay reagents of this invention to provide reagents that generate individual amplifiable signals. Reagents containing such variant DNA with inserted DNA sequences can be used in methods of this invention to detect, or to detect and quantitate, simultaneously two or more analytes in a test sample.

Immunoassay test kits are also disclosed. Such immunoassay test kits comprise immunoassay regents of this invention and an apropriate RNA-dependent RNA polymerase, wherein the variant DNA of the reagents is a substrate for the polymerase. Such test kits can further comprise a solid phase to which an anti-analyte antibody or a receptor for the analyte under assay is attached. Other embodiments of such immunoassay test kits can comprise variant DNA conjugated to avidin, preferably streptavidin, and/or Protein A.

Abbreviations

ATP—adenosine triphosphate
CDR—complementarity determining region
cpm—counts per minute
CTP—cytidine triphosphate
dATP—deoxyadenosine triphosphate
dCTP—deoxycytidine triphosphate
dGTP—deoxyguanosine triphosphate
DNA—deoxyribonucleic acid
DTT—dithiothreitol
dTTP—deoxythymidine triphosphte
EDC—1-ethyl-3-(3-diethylaminopropyl) carbodiimide
EDTA—ethylenediaminetetraacetic acid
GTP—guanosine triphosphate
hr—hour
M—molar
MBS—m-maleimidobenzoyl N-hydroxysuccinimide ester
ml—milliliter
mM—millimolar
nmol—nanomole
PBS—phosphate buffered saline [50 mM $NaPO_4$, 150 mM NaCl]
PBSE—PBS with 1 MM EDTA
PMP—paramagnetic particle
RNA—ribonucleic acid
SMCC—succinimidyl 4-(N-maleimido-methyl) cyclohexane-1-carboxylate
SPDP—N-succinimidyl-3-(2-pyridylthio)-propionate
UTP—uridine triphosphate
$\mu$M—micromolar
$\mu$g—microgram

DETAILED DESCRIPTION

Aspects of this invention revolve around antibody-variant DNA conjugates that are immunoassay reagents. The conjugates are components of an immunoassay signal amplification system.

For enhanced sensitivity of immunoassays, the signal for an analyte molecule, especially when the analyte is in trace concentrations, needs to be amplified, so that the signal is visualizable and thus detectable. The instant invention provides such a signal amplification system. The system can produce an amplified signal representative of the number of analyte molecules in a sample that is assayed by methods of this invention.

The variant DNA of the conjugates when bound to an immunocomplex according to this invention is transcribed to RNA, and then the RNA transcripts are replicated, by contact with an appropriate RNA-dependent RNA polymerase in the presence of ribonucleotides, resulting in RNA replication products. Thus, for each bound variant DNA template molecule transcribed, many RNA variant molecules can be produced. Those RNA replication products are rendered visualizable by an appropriate means, such as by labeling with a radionuclide, fluorescer, chemiluminescer, or enzyme or by staining with an intercalating dye, among other methods (as discussed infra).

Examples 1–3, below demonstrate some representative methods of preparing the antibody-variant DNA conjugates of this invention.

Example 4 demonstrates the ability of variant DNA conjugated to an antibody to serve as a template for an RNA-dependent RNA polymerase to synthesize RNA. In Example 4, nanovariant DNA conjugated to antibodies via the representative cross-linking reagent SPDP, retains its capability to serve as a template for QB replicase catalyzed synthesis of nanovariant RNA. Thus, evidence is provided to show that representative antibody-variant DNA conjugates of this invention, may be used for immmunoassays of enhanced sensitivity.

The overall antibody concentration is chosen so that the amount of conjugated antibody non-specifically bound and capable of amplification by a RNA-dependent RNA polymerase, such as, QB replicase, is approximately 1000 to 10,000 molecules. The current replication sensitivity of a nanovariant DNA or midivariant DNA template in solution has been found by the inventors to be approximately 10,000 molecules. Since levels of DNA template below that level do not appear to yield detectable levels of RNA synthesis, no background signal may be expected from that level of non-specific binding. Thus 1000 to 10,000 molecules would be the theoretical limit of sensitivity for the immunoassays of this invention.

One can control the sensitivity of the system to some degree by varying the concentration of the conjugate and other key factors, such as the concentration of antibody, the amount of polymerase, and the detection method. A specific immunoassay can be optimized by methods known to those of skill in the art.

After the binding of an analyte directly or indirectly to the antibody-variant DNA conjugate, binding to a second reagent, such as, a second antibody attached to a solid phase would take place as in conventional immunoassay formats. Such a solid phase reagent facilitates the separation of the bound and unbound antibody-conjugate.

A particularly prepared solid phase comprises a paramagnetic particle (PMP) [Ciba Corning Diagnostics Corp.; Medfield, Mass. (USA)]. PMPs are paramagnetic. If capture antibody or receptor to the analyte under assay are attached to such PMPs, captured immunocomplexes can be separated from unbound antibody-variant DNA conjugates by applying a magnetic field.

After separation and wash as in conventional immunoassays, the solid phase with the adsorbed antibody conjugate is incubated with an RNA-dependent RNA polymerase, such as, QB replicase to provide the amplified signal. The variant RNA, such as nanovariant RNA or midivariant RNA, synthesized in that amplification step is produced in sufficient quantities to render it detectable by a variety of methods, radioactive or non-radioactive, as are conventionally used.

A preferred embodiment for practicing this invention would include, for example, incubating a test sample containing the analyte to be detected, or, to be detected and quantitated, with an antibody which binds specifically to the analyte and is conjugated with nanovariant or midivariant DNA for an appropriate amount of time. Another preferred embodiment would be to mix a small amount of such an antibody-variant DNA conjugate according to this invention with unconjugated antibody that is specific for the analyte to be determined. Thus, in that embodiment, the amount of analyte bound by antibody is maintained, but the amount of label is reduced, thereby reducing the level of potential background signal. The conjugated DNA templates serve as amplifiable labels to enable the detection of trace amounts of an analyte.

An exemplary immunoassay method of this invention for detecting, or, for detecting and quantitating an analyte in a test sample comprises the steps of:

(a) contacting said test sample with an antibody-variant DNA conjugate, wherein the antibody of the conjugate is either specific for the analyte under assay or for a second antibody added to said test sample that is specific for the analyte under assay, and wherein the variant DNA of the conjugate is a substrate for an RNA-dependent RNA polymerase;

(b) incubating said test sample with said antibody-variant DNA conjugate and said second antibody, if present, for an appropriate amount of time;

(c) removing antibody-variant DNA conjugate which is not bound to the analyte under assay;

(d) transcribing the variant DNA of conjugate that is bound to the analyte, to RNA, and replicating the RNA transcripts, by contacting the variant DNA template and RNA transcripts with a sufficient amount of an appropriate RNA-dependent RNA polymerase in the presence of ribonucleotides; and (e) determining whether any variant RNA is replicated in step (d) and correlating the presence of RNA replication products with the presence of analyte; or detecting and quantitating variant RNA replicated in step (d), and correlating the quantity of said RNA replication products with the quantity of analyte.

Such a method can further comprise before step (c) or simultaneously with step (c), contacting said test sample with a receptor for said analyte, or with an additional anti-analyte antibody which is directed to a different epitopic site on said analyte than to that which said second antibody, if present, is directed, or than to that which the conjugate antibody is directed, if said conjugate antibody is directed to an epitopic site on said analyte.

The analyte receptor or said anti-analyte antibody of such preferred embodiments can be immobilized upon a solid phase. Exemplary of an analyte receptor are estrogen receptors, progesterone receptors, growth factor receptors, among many others.

Two or More Analytes

Another preferred embodiment is that wherein two or more analytes in a test sample are detected, or detected and quantitated simultaneously. Two or more different antibody-variant DNA conjugates are used in such an embodiment, wherein the variant DNA of different conjugates comprise different DNA sequences inserted therein, preferably at a position other than within 10 bases from the 3' end of the variant DNA, more preferably other than within 20 bases from the 3' end.

Such inserted DNA sequences are sequences whose RNA counterparts do not naturally occur in variant RNA templates that are substrates for RNA-dependent RNA polymerases, such as, QB replicase. More preferably, such inserted sequences are non-variant DNA. [See, Martinelli et al., European Patent Application Publication No. 481,704 entitled "Amplification of midivariant templates," (published Apr. 22, 1992).]

The lengths of such inserted DNA sequences can be from about 10 nucleotides to about 120 nucleotides. Preferably, the variant DNA is nanovariant or midivariant DNA, wherein the lengths of the inserted DNA sequences are preferably from about 10 nucleotides to about 50 nucleotides, more preferably from about 10 nucleotides to about 30 nucleotides.

Midivariant DNA is particularly preferred according to this invention for inserting therein different DNA sequences. Inserted DNA sequences, that have no RNA counterparts naturally occuring in midivariant RNA, which is a template for QB replicase, having lengths of from about 10 to about 120 bases, have been found to be transcribed and replicated successfully from midivariant DNA. Such sequences are preferably inserted in a midivariant DNA template at a position about in the middle of the midivariant DNA, or at a position about one quarter of the length of the midivariant DNA from the 5' end, that is, from about 55 to 70 bases from the 5' end. Further preferred is that such inserted DNA sequences be inserted at a position in the positive strand of the midivariant DNA [MDV-1 (+) DNA] at about nucleotides 130 to 131, or at about nucleotides 61 to 64, more preferably at nucleotide 63.

An embodiment of such assays for detecting, or for detecting and quantitating, simultaneously two or more different analytes in a test sample, is that wherein the antibodies conjugated to variant DNA containing different inserted DNA sequences are specific for different analytes, whereas antibodies conjugated to variant DNA containing the same inserted DNA sequences are specific for the same analyte. Ones of skill in the art realize that other functional equivalents of using such anti-analyte antibodies, for example, equivalents analogous to those described herein when one analyte is under assay, can be successfully used according to this invention.

In assays of this invention to detect, or to detect and quantitate, two or more analytes simultaneously, the different variant DNAs, when bound respectively in immunocomplexes to different analytes, are transcribed, and the RNA transcripts are replicated, by contact with an appropriate RNA-dependent RNA polymerase. The different variant RNA replication products can be detected by hybridization to differently labeled nucleic acid probes, preferably RNA probes. Preferably the probes are complementary to the RNA counterparts of the DNA sequences inserted within the variant DNA of the conjugates.

The probes hybridize under standard hybridization conditions, to the variant RNA replication products. Varying conditions of hybridization may be desired, depending on, for example, the specific immunoassay envisioned, the number of analytes to be detected or the selectivity of the probe towards the target RNA replication product sequence. Where a high degree of selectivity is desired, one may employ relatively stringent hybridization conditions, such as, relatively low salt and/or high temperature conditions. Under such conditions, relatively little mismatch between the probe and the target sequence is tolerated. Less stringent conditions may usually be desired when optimizing conditions for a specific immunoassay.

Thus, a representative embodiment of a method according to this invention for detecting, or for detecting and quantitating, two or more analytes simultaneously in a test sample comprises performing the exemplary immunoassay, outlined above in relation to a single analyte, simultaneously with two or more different antibody-variant DNA conjugates, wherein the antibody-variant DNA conjugates differ in that the variant DNA of the different conjugates comprise different DNA sequences inserted therein. In the context of a specific immunoassay, the DNA sequences inserted in the variant DNA are the same when conjugated to antibodies having similar binding specificities, whereas the inserted DNA sequences are different in variant DNAs conjugated to antibodies having different binding specificities.

Further, an exemplary immunoassay method of this invention for detecting, or detecting and quantitating, two or more analytes simultaneously in a test sample comprises the steps of:

(a) contacting said test sample with two or more different antibody-variant DNA conjugates, wherein the variant DNA of different conjugates comprises different DNA sequences inserted therein; wherein the antibodies conjugated to variant DNA containing different inserted DNA sequences are specific for different analytes, whereas the antibodies conjugated to variant DNA containing the same inserted DNA sequence are specific for the same analyte; and wherein the variant DNA of said conjugates is a substrate for an RNA-dependent RNA polymerase;

(b) incubating said test sample with said two or more different antibody-variant DNA conjugates for an appropriate amount of time;

(c) removing antibody-variant DNA conjugates which are not bound to an analyte under assay;

(d) transcribing the variant DNA and the inserted DNA sequences of the conjugates that are bound to analytes, to RNA, and replicating the RNA transcripts, by contacting said variant DNA templates and RNA transcripts with a sufficient amount of an appropriate RNA-dependent RNA polymerase in the presence of ribonucleotides; and (e) determining whether any variant RNA is replicated in step (d), and, if so, determining from which variant DNA template or templates, said variant RNA was transcribed, and correlating the presence of RNA replication products generated from a certain variant DNA template with the presence of the corresponding analyte, that is, the analyte, for which the antibody to which that certain variant DNA is conjugated is specific; or determining from which variant DNA template or templates, said variant RNA replicated in step (d) was transcribed, quantitating each of the different variant RNA replication products, and correlating the quantity of each of the RNA replication products with the quantity of each corresponding analyte.

The different variant RNAs replicated from the different variant DNA templates are preferably detected in step (e) by employing two or more differently labeled nucleic acid probes that are complementary to the different variant RNAs that are replicated, and wherein the probes that are complementary to one type of replicated variant RNA are similarly labeled. Preferably, the differently labeled nucleic acid probes are RNA probes, and are complementary respectively to the different DNA sequences inserted in said different variant DNAs.

Universal Reagents

An antibody-variant DNA conjugate of this invention can be a universal immunoassay reagent or can be directed against a specific analyte. Embodiments wherein the antibody-variant DNA conjugate is a universal type reagent may be preferred for certain immunoassays.

An exemplary universal reagent would be that wherein the antibody of the conjugate is directed against antibodies that originated by immunizing a mammal of a different genus, than that from which the conjugate antibody originated. For example, the antibody of the conjugate could be a goat anti-mouse antibody, and thus be useful as a component of a signal amplification system for any immunoassay employing mouse antibodies. Also included within the scope of such universal reagents are antibodies functionally equivalent to such antibodies, as represented by a goat anti-mouse antibody, as, for example, those that are genetically engineered or otherwise prepared, and biologically active antibody fragments.

Another embodiment wherein the antibody-variant DNA conjugate can be considered to be a universal type of immunoassay reagent is that wherein the variant DNA is linked to avidin, and biotinylated anti-analyte antibodies are used. In that embodiment, the universal immunoassay reagent is actually the variant DNA linked to avidin, preferably the variant DNA linked to streptavidin. The variant DNA-antibody conjugate in that embodiment is prepared during the immunoassay procedure.

Details concerning various aspects of the invention follow.

General Methods

Reference is hereby made to standard textbooks of molecular biology and immunology that contain definitions and methods for carrying out basic techniques of the present invention, such as, immunoassay techniques, RNA-dependent RNA polymerase mediated amplification protocols, detection of amplified nucleic acids, and the mechanism and methodology of autocatalytic replication. See, for example, Sambrook et al., *Molecular Cloning: A Laboratory Manual* (2nd Ed.) Cold Spring Harbor Laboratory Press (1989); Darnell et al., *Molecular Cell Biology*, W. H. Freeman and Company (N.Y. 1990); Colowick et al.,

*Methods in Enzymology,* Volume 152 [Academic Press, Inc. (London) Ltd. (1987)]; and Goding, J. W., *Monoclonal Antibodies: Principles and Practice: Production and Application of Monoclonal Antibodies in Cell Biology, Biochemistry and Immunology* [Academic Press Inc. (London) Ltd.; 1983.]

RNA-dependent RNA Polymerases

RNA-dependent RNA polymerases are herein sometimes referred to as "replicases." It is generally considered known in the art is that such replicases are enzymes that replicate, that is, reproduce, RNA transcripts and their complements so as to multiply copies thereof. When a replicase is present during the process of transcription, it can be forseen that the multiple transcripts that are produced during transcription can themselves undergo replication so as to increase exponentially the amount of RNA transcript product.

A replicase functions to replicate exponentially an RNA transcript as long as the replicase is in molar excess over the RNA strands produced. The variant DNA of the conjugate of this invention thus serves as a template for the synthesis of a complementary RNA strand. After N rounds of replication, there will be $2^N$ strands produced for each initial template strand.

Conditions for using replicases are will known in the art. See, for example, Kramer et al., *J. Mol. Biol.,* 89: 719 (1974; and Lizardi et al., *Bio/Technology,* 6: 1197 (1988).

RNA replicases have been isolated from *Escherichia coli* RNA phages [Lewin, B. in *Gene Expression,* 3: 790–824 (John Wiley & Sons; 1977)]; from plant RNA viruses [Miller et al., *J. Mol. Biol.,* 187: 537 (1986)], and as a secondary catalytic activity present in T7 RNA polymerase [Konarska and Sharp, *Cell,* 57: 427 (1989)]. QB replicase is the best characterized of the RNA replicases.

QB replicase is a particularly preferred replicase for use in the immunoassay methods of this invention. [See, Miele et al., "Autocatalytic Replication of a Recombinant RNA," *J. Mol. Biol.,* 171: 281 (1983).] QB replicase can be isolated from bacteriophage QB-infected *Escherichia coli,* by the procedure of Eoyang and August in *Procedures in Nucleic Acid Research,* 2: 829–839, [eds. Cantoni and Davies (Harper and Row, N.Y.; 1971)].

The QB virus is an RNA phage of approximately 4400 ribonucleotides. [See, Blumenthal in *The Enzyme,* Vol. XV, Part B, p. 267, ed. P. D. Boyer (Academic Press, N.Y.; 1982).] Although QB replicase replicates only QB RNA and not other viral RNA sequences, shorter, RNA sequences can also serve as templates for replication. Those shorter templates include "nanovariant" RNA which is 90 ribonucleotides in length and "midivariant" RNA which is 220 ribonucleotides in length.

Midivariant RNA, MDV-1, has been extensively characterized and found to contain specific sequences and structures necessary for replication. "A single molecule of MDV-1 RNA is sufficient to initiate an exponential replication reaction . . . in which the number of RNA strands is duplicated every 30 seconds as long as the enzyme remains in excess." [Lizardi and Koramer, *TibTech,* 9: 53 at page 54 (February 1991).]

Other RNA-dependent RNA-polymerases that can be used as part of the signal amplification system of the immunoassays of this invention include the RNA phage replicases SP, MS2 and GA. [See, Mills et al., *J. Mol. Biol.,* 205: 751 (1988).] Another replicase that may be useful in the methods of this invention is the Brome Mosaic Virus replicase. [March et al., *Positive Strand RNA Viruses* (Alan R. Liss; N.Y.; 1987).] Other replicases and their associated substrates, can be found in Miyake et al., *PNAS* (USA), 68: 2022 (1971).

Antibody-Variant DNA Conjugates (1) Variant DNA

Variant DNAs correspond to variant RNAs which are substrates for replicases. For example, midivariant DNA corresponds to midivariant RNA. [See Miele et al., *J. Mol. Biol.,* 171: 281 (1983).] Preferred variant DNAs according to this invention are nanovariant, midivariant, microvariant and minivariant DNAs; more preferred are nanovariant and midivariant DNAs, most preferably those that are substrates for QB replicase; and further preferred are nanovariant DNAs that are substrates for QB replicase.

(2) Antibody

The term "antibodies" is defined herein to include not only whole antibodies but also biologically active fragments of antibodies, preferably fragments containing the antigen binding regions. Such antibodies may be prepared by conventional methodology and/or by genetic engineering. Antibody fragments may be genetically engineered, preferably from the variable regions of the light and/or heavy chains ($V_H$ and $V_L$), including the hypervariable regions, and still more preferably from both the $V_H$ and $V_L$ regions.

Thus, the term "antibodies" as used herein comprehends polyclonal and monoclonal antibodies and biologically active fragments thereof including among other possibilities "univalent" antibodies [Glennie et al., *Nature,* 295: 712 (1982)]; Fab proteins including Fab' and F(ab')$_2$ fragments whether covalently or non-covalently aggregated; light or heavy chains alone, preferably variable heavy and light chain regions ($V_H$ and $V_L$ regions), and more preferably including the hypervariable regions [otherwise known as the complementarity determining regions (CDRs) of said $V_H$ and $V_L$ regions]; $F_c$ proteins; "hybrid" antibodies capable of binding more than one antigen; constant-variable region chimeras; "composite" immunoglobulins with heavy and light chains of different origins; "altered" antibodies with improved specificity and other characteristics as prepared by standard recombinant techniques and also by oligonucleotide-directed mutagenesis techniques [Dalbadie-McFarland et al., *PNAS* (USA), 79: 6409 (1982)].

It may be preferred for many immunoassays of this invention that biologically active fragments rather than whole antibodies be used. Fab fragments are particularly preferred fragments in accordance with this invention to avoid non-specific binding.

Antibodies for use in the instant invention can be genetically engineered. [See, for example, Morrison et al., *Clin. Chem.,* 34: 1668 (1988); Morrison and Oi, *Adv. Immunol.,* 44: 65 (1989); Rodwell, *Nature,* 342: 99 (1989); Pluckthun, A., *Nature,* 347: 497 (1990); Winter and Milstein, *Nature,* 349: 293 (1991); Pluckthun, A., *Bio/Technology,* 9: 545 (1991); Wetzel, R., *Protein Eng.,* 4: 371 (1991); Geisow, M. J., *Trends Biotechnol.,* 10: 75 (1992); and Chiswell and McCaffery, *Trends Biotechnol.* 10: 85 (1992).] Further bispecific and other types of antibodies [for example, Lerner and Tramanto, *Trends Biochem. Sci.,* 12: 427 (1987); Shokat and Schultz, *Annu. Rev. Immunol.,* 8: 335 (1990); Schultz, P. G., *Science,* 240: 426 (1988); Benkavic et al., *Science,* 250: 1135 (1990); and Lerner et al., *Science,* 252: 659 (1991); Noland and O'Kennedy, *Biochem. Biophys. Acta.,* 1040: 1 (1990); and Bolhuis et al., *Cell Biochem.,* 47: 306 (1991)] can also be conjugated to replicable variant DNA templates for use according to this invention.

(3) Preparation of Conjugates

Conjugation methods known by those of skill in the art can be used to prepare the antibody-variant DNA conjugates of this invention. [See, for example, Goding, J. W., supra.] Two general approaches to prepare antibody-variant DNA conjugates of this invention are shown in Examples 1 and 2 below.

In one such approach, as detailed in Example 1, a derivative of nanovariant DNA, such as PM444 (SEQ. ID. NO.: 1) [Promega; Madison, Wis. (USA)], containing a primary amine was conjugated to mildly reduced antibodies via a heterobifunctional group, such as SPDP. In a second such general approach, as detailed in Example 2, an amino-derivatized nanovariant DNA can be coupled to an antibody's amine groups by using a heterobifunctional group, such as SPDP.

Preferred, as exemplified in Example 3, is to prepare an amino-derivatized variant DNA wherein the amino group is at the 5' end. RNA replicases, such as, QB replicase, initiate product strand synthesis at the 3' end. Further preferred methods for preparing such an amino-derivatized variant DNA comprise the use of a DNA synthesizer.

Other coupling agents, preferably heterobifunctional linking agents, known to those in the art, include m-maleimidobenzoyl N-hydroxysuccinimide ester [Kitagawa, T. in *Enzyme Immunoassay* (eds. Ishikawa et al.) (Igaku-Shoin; Tokyo and New York; 1981)] or related compounds, carbodiimides, such as, 1-ethyl-3-(3-diethylaminopropyl) carbodiimide (EDC), among others, succinimidyl 4-(N-maleimido-methyl) cyclohexane-1-carboxylate (SMCC), and glutaraldehyde cross-linkers, can be used to prepare the antibody-variant DNA conjugates of this invention.

Further, other methods known to those of skill in the art can be used to prepare the antibody-variant DNA conjugates of this invention. For example, a variant DNA, preferably nanovariant or midivariant DNA, could be conjugated to avidin, preferably streptavidin, and then linked to biotinylated antibodies. Further, for example, by a method analogous to that described in Chu et al., supra, biotin could be attached to the 5' terminus of midivariant or nanovariant DNA via a disulfide linker, and the biotinylated DNA could be combined with avidin to form a DNA-biotin-avidin adduct, which then could be conjugated to biotinylated antibodies. Other methods of attaching avidin to variant DNA are known to those in the art such as methods employing Protein A. [See, for example, Sano et al., *Science* 258: 120 (Oct. 2, 1992).]

Detection and Quantitation of Replication Products

There are many conventional means to detect the RNA replication products produced by the immunoassay methods of this invention. They include the incorporation of radioactive labels, e.g. Harper et al., *Chromosoma*, 83: 431–439 (1984); direct attachment of fluorochromes or enzymes, e.g. Smith et al., *Nuc. Acids Res.*, 13: 2399–2412 (1985), and Connolly et al., *Nuc. Acids Res.*, 13: 4485–4502 (1985); and various chemical modifications of nucleic acids that render them detectable immunochemically or by other affinity reactions, e.g. Tchen et al., "Chemically Modified Nucleic Acids as Immunodetectable Probes in Hybridization Experiments," *PNAS,* 81: 3466–3470 (1984); Richardson et al., "Biotin and Fluorescent Labeling of RNA Using T4 RNA Ligase," *Nuc. Acids Res.*, 11: 6167–6184 (1983); Langer et al., "Enzymatic Synthesis of Biotin-Labeled Polynucleotides: Novel Nucleic Acid Affinity Probes," *PNAS,* 78: 6633–6637 (1981); Brigati et al., "Detection of Viral Genomes in Cultured Cells and Paraffin-Embedded Tissue Sections Using Biotin-Labeled Hybridization Probes," *Virol.,* 126: 32–50 (1983); Broker et al., "Electron Microscopic Visualization of tRNA Genes with Ferritin-Avidin: Biotin Labels," *Nuc. Acids Res.,* 5: 363–384 (1978); Bayer et al., "The Use of the Avidin Biotin Complex as a Tool in Molecular Biology," *Methods of Biochem. Analysis,* 26: 1–45 (1980); Kuhlmann, *Immunoenzyme Techniques in Cytochemistry* (Weinheim, Basel, 1984); Langer-Safer et al., *PNAS* (USA), 79: 4381 (1982); Landegent et al., *Exp. Cell Res.,* 153: 61 (1984); and Hopman et al., *Exp. Cell Res.,* 169: 357 (1987).

Exemplary detection means include the use of labels, such as, radionuclides, enzymes, coenzymes, fluorescers, chemiluminescers, chromogens, enzyme substrates, enzyme co-factors, enzyme inhibitors, free radicals, particles, dyes and the like. Further, exemplary labeling means include those wherein the RNA replication products are biotinylated, modified with N-acetoxy-N-2-acetylaminofluorene, modified with fluorescein isothiocyanate, sulfonated, digoxigeninated, modified to contain T-T dimers or stained with an intercalating dye.

In a preferred embodiment, the RNA replication products are detected by chemiluminescent methodology. See U.S. Pat. No. 4,745,181. The use of acridinium ester as a chemiluminescer is particularly preferred.

Example 4 details a representative detection means wherein radioactively labeled ribonucleotides ($^{32}$P-CTPs) are incorporated in the RNA replication products. Analogously, fluorochromes, enzymes or other labels may be incorporated in the replication products. Another exemplary method for incorporating fluorescent nucleotides in replicated RNA is shown in Cosstick et al., *Nuc. Acids Res.,* 12: 1791 (1984).

Also, electrophoretic means, such as, the use of polyacrylamide gel electrophoresis, could be used to detect and/or quantitate the RNA replication products. [See, for example, Sano et al., *Science,* 258: 120 (Oct. 2, 1992).]

Another detection methodology incorporates the use of optical devices to propagate radiation by "total internal reflection" to generate an evanescent wave at the interface of the device and a test medium having a lower index of refraction. See Harrick, N.J., *Internal Reflection Spectroscopy* (Harrick Scientific Corp; N.Y.; 3rd printing 1987); and U.S. Pat. No. 4,880,752.

According to this invention, the signal generated from the replication products indicates the presence of the analyte under assay. That signal may also be used to quantitate the amount of the analyte present in the assay by methods known to those of skill in the art.

For example, under conditions of replicase enzyme excess, the amount of time it takes to synthesize a particular, though arbitrary, mass of amplified RNA from the variant DNA templates is directly related to the logarithm of the number of DNA molecules present at the start of the assay (time zero). The amount of amplified RNA can be measured, for example, by the florescence of an intercalating dye, such as, ethidium bromide. There is a semilogarithmic relationship between the amount of DNA template present in an assay and the amount of RNA synthesized by a replicase enzyme.

Immunoassay Formats

It is apparent to one of skill in the art that the signal amplification system of this invention can be used in a variety of immunoassay formats, such as, sandwich assays, competition assays, bridge immunoassays, among other formats well known to those of skill in the art. [See, for example, U.S. Pat. Nos. 5,296,347; 4,233,402; 4,034,074; and 4,098,876.]

The following examples are presented to help in the better understanding of the subject invention and are for purposes of illustration only. The examples are not to be construed as limiting the invention in any manner.

EXAMPLE 1

The nanovariant DNA used in the examples described herein is PM444 [Promega]. PM444 has the following nucleotide sequence:

GGGGAAATCC TGTTACCAGG ATAACGGGGT TTTCTCACCT CTCTACTCGA AAGTTAGAGA GGACACACCC GGATCTAGCC GGGTCAACCC [SEQ. ID. NO.: 1].

A primary amine group was introduced into PM444 at its 3' terminus using terminal transferase with either aminohexyl-ATP or a combination of aminohexyl-ATP and dATP. The product of this reaction was labeled at its 5' terminus with $^{32}P$ with polynucleotide kinase and gamma $^{32}P$-ATP.

PM444 with a 5' $^{32}P$ and 3' aminohexyl-ATP (20 nM) was incubated with N-succinimidyl-3-(2-pyridylthio)propionate (SPDP)(100 uM) [Pharmacia; Uppsala, Sweden] at room temperature for 1 hr. The SPDP-derivatized oligomer was desalted on Sephadex G25 [Pharmacia] in 50 mM $NaPO_4$, 150 mM NaCL (PBS).

A monoclonal antibody directed against an RNA-DNA hybrid (100 nM) was reduced with dithiothreitol (DTT) (20 mM) at room temperature for 30 min in 50 mM $NaPO_4$, 150 mM NaCL, 1 mM EDTA (PBSE). The reduced antibody was desalted on Sephadex G-25 in PBSE.

The SPDP-derivatized oligomer was incubated with the reduced antibody at room temperature overnight. The antibody-DNA conjugate formed in this reaction was purified by affinity chromatography on Affigel Protein A [Biorad; Hercules, Calif. (USA)]. $^{32}P$ labeled oligomer which bound to the column did so by virtue of its conjugation to the antibody. Bound material was eluted from the column with 0.1 M sodium citrate, pH 3 and neutralized by the addition of 1 M Tris, pH 9. The fractions containing $^{32}P$ were identified by liquid scintillation counting.

EXAMPLE 2

Anti-RNA-DNA hybrid monoclonal antibody (15 $\mu M$) and SPDP (100 $\mu M$) were reacted at room temperature for 1 hr. The derivatized antibody was desalted on Sephadex G25.

The amino-oligomer (10 nM), that is, the amino derivatized PM444 as prepared in Example 1, was also incubated with SPDP (100 $\mu M$) at room temperature for 1 hr. To that solution, DTT was added to give a final concentration of 0.1 M, and reduction proceeded for 10 minutes. The thiol-derivatized oligomer resulting from the reaction was desalted on Sephadex G-25.

The oligomer was then incubated with the SPDP-derivatized antibody at room temperature overnight. The antibody-oligomer conjugate formed was purified by affinity chromatography on Affigel Protein A as described above in Example 1.

EXAMPLE 3

A version of PM444 containing an amine group at its 5' terminus was prepared, and labeled at its 3' terminus with $^{32}P$-dideoxy-ATP with terminal transferase. That version of PM444, called PM653 [Promega], was also coupled to antibody via SPDP by using each of the methods described above in Examples 1 and 2.

EXAMPLE 4

The ability of antibody-conjugated variant DNA to serve as a template for QB replicase catalyzed synthesis of variant RNA was examined. Exemplary of such antibody-conjugated variant DNA is the antibody-conjugated nanovariant DNA, that is, the antibody-PM444 conjugates, prepared as described in Examples 1 and 2.

The antibody-PM444 conjugates were incubated with QB replicase (20 $\mu g$/ml) in 100 mM Tris, pH 7.5, 15 mM $MgCl_2$, 1 mM each ATP, GTP, CTP, and UTP, at room temperature. The reaction also contained alpha $^{32}P$-CTP sufficient to give $2.6\times10^5$–$4.28\times10^5$ cpm/nmol CTP. Incorporated CTP was detected by precipitation of the RNA product onto glass fiber filters [Whatman International; Kent, England] in the presence of 10% trichloroacetic acid/1% sodium pyrophosphate.

As controls to determine whether RNA synthesis was due to contamination by nanovariant RNA, either no antibody conjugate was added to the replicase reactions, or the antibody conjugates were digested with deoxyribonuclease [DNAse; Promega] at 37° C. for 1 hr prior to addition to the replicase reaction.

The results of the experiments are summarized in Table I. In each case, the antibody-nanovariant DNA conjugate was capable of serving as a template for RNA synthesis. Treatment of the conjugates with DNAse significantly reduced the amount of RNA synthesized. The results shown in Table I are consistent with the ability of nanovariant DNA to serve as a template for RNA synthesis even while conjugated to an antibody.

TABLE I

Synthesis of Nanovariant RNA from Antibody-Nanovariant DNA Conjugates

| Template Added | CTP Incorporated nmoles |
| --- | --- |
| Zero | 0.005 |
| Antibody-PM444 | 0.62 |
| Antibody-PM444 + DNAse | 0.11 |
| PM444 | 1.65 |
| PM444 + DNAse | 0.07 |

The description of the foregoing embodiments of the invention have been presented for purposes of illustration and description. They are not intended to be exhaustive or to limit the invention to the precise form disclosed, and obviously many modifications and variations are possible in light of the above teachings. The embodiments were chosen and described in order to explain the principles of the invention and its practical application, and thereby to enable others skilled in the art to utilize the invention in various embodiments and with various modifications as are suited to the particular use contemplated. It is intended that the scope of the invention be defined by the claims appended hereto.

All references cited herein are hereby incorporated by reference.

We claim:

1. An immunoassay method to detect or detect and quantitate an analyte in a test sample comprising:
   (a) contacting said test sample with a conjugate of an antibody coupled to variant DNA as a component of a signal amplification system, wherein said variant DNA is a substrate for an RNA-dependent RNA polymerase, and wherein said antibody is either specific to the analyte under assay or is specific to another antibody or to an immunocomplex that is specific to the analyte under assay;
   (b) incubating said conjugate with said test sample, or incubating said conjugate with said test sample and with said other antibody or immunocomplex that is specific to the analyte under assay for an appropriate amount of time;
   (c) separating any conjugate that is bound to analyte, either directly or through said other antibody or said immunocomplex, from conjugate that is not bound to an analyte;
   (d) transcribing said variant DNA of conjugate that is bound to the analyte, to RNA, and replicating the RNA transcripts, by contacting said variant DNA template and RNA transcripts with a sufficient amount of both an appropriate RNA-dependent RNA polymerase and ribonucleotides; and
   (e) determining whether any variant RNA is replicated in step (d) and correlating RNA replication products with analyte being present in said test sample; or detecting and quantitating variant RNA replicated in step (d), and correlating the quantity of said RNA replication products with that of analyte present in said test sample.

2. The method of claim 1 wherein said variant DNA is selected from the group consisting of nanovariant, midivariant, microvariant, and minivariant DNAs, and wherein said RNA-dependent RNA polymerase is selected from the group consisting of RNA phage replicases and Brome Mosaic Virus replicase.

3. The method of claim 2 wherein said variant DNA is either nanovariant DNA or midivariant DNA; and wherein said RNA-dependent RNA polymerase is selected from the group consisting of QB replicase, SP replicase, MS2 replicase and GA replicase.

4. The method according to claim 1 wherein the antibody of said conjugate is either a monoclonal antibody or a Fab fragment; and wherein said RNA-dependent RNA polymerase is QB replicase.

5. The method of claim 1 wherein said antibody of said conjugate binds to antibodies that originated by immunizing a mammal of a different genus than the mammal from which said antibody of said conjugate originated.

6. The method of claim 1 wherein said variant DNA is conjugated to said antibody by forming a biotin-avidin bridge or a biotin-avidin-protein A bridge between said antibody and said variant DNA, or by preparing said antibody-variant DNA conjugate with a heterobifunctional linking agent.

7. An immunoassay method to detect, or to detect and quantitate, two or more analytes in a test sample simultaneously, comprising:
   (a) contacting said test sample with two or more different conjugates, each comprising an antibody coupled to a variant DNA, wherein said variant DNA of a conjugate that is different from another conjugate contains a DNA sequence inserted therein that is not present in said variant DNA of said different conjugate, and wherein said antibody of a conjugate that is different from another conjugate binds either directly or indirectly to a different analyte than said antibody of the different conjugate, and wherein each of said variant DNAs is a substrate for an RNA-dependent RNA polymerase;
   (b) incubating said test sample with said two or more different conjugates for an appropriate amount of time;
   (c) removing conjugates which are not bound to an analyte under assay;
   (d) transcribing said variant DNA and said inserted DNA sequences of the conjugates that are bound to analytes, to RNA, and replicating said RNA transcripts, by contacting said variant DNA templates and RNA transcripts with a sufficient amount of both an appropriate RNA-dependent RNA polymerase and ribonucleotides; and
   (e) determining whether any variant RNA is replicated in step (d), and, if so, determining from which variant DNA template or templates, said variant RNA was transcribed, and correlating the presence of RNA replication products generated from a certain variant DNA template of a conjugate, with the presence of the corresponding analyte in said test sample; or determining from which variant DNA template or templates, said variant RNA replicated in step (d) was transcribed, quantitating each variant RNA replication product, and correlating the quantity of each variant RNA replication product with said quantity of the corresponding analyte.

8. The method according to claim 7 wherein step (e) comprises using two or more different nucleic acid probes, wherein each of said probes is complementary to said variant DNA of one of said two or more different antibody-variant DNA conjugates; wherein said probes that are complementary to the variant DNA of the conjugates that are specific for the same analyte are similarly labeled; and wherein said probes that are complementary to said variant DNA of the conjugates that are specific for different analytes are differently labeled from each other.

9. The method according to claim 7 wherein said variant DNA of said antibody-variant DNA conjugates is conjugated to said antibody of said conjugates through an avidin-biotin or streptavidin-biotin bridge, via Protein A or by means of a heterobifunctional linking agent.

10. An immunoassay method for detecting an analyte in a test sample, or for detecting and quantitating an analyte in a test sample comprising:
(a) contacting said test sample with a conjugate of an antibody coupled to variant DNA, wherein said antibody of the conjugate is either specific for the analyte under assay or for a second antibody added to said test sample that is specific for the analyte under assay, and wherein said variant DNA of the conjugate is a substrate for an RNA-dependent RNA polymerase;
(b) incubating said test sample with said conjugate and said second antibody, if present, for an appropriate amount of time;
(c) removing conjugate which is not bound to the analyte under assay;
(d) transcribing said variant DNA of conjugate that is bound to the analyte, to RNA, and replicating said RNA transcripts, by contacting said variant DNA template and RNA transcripts with a sufficient amount of both an appropriate RNA-dependent RNA polymerase and ribonucleotides; and
(e) determining whether any variant RNA is replicated in step (d) and correlating RNA replication products with analyte being present in said test sample; or detecting and quantitating variant RNA replicated in step (d), and correlating the quantity of said RNA replication products with that of analyte present in said test sample.

11. The method according to claim 10 further comprising before step (c) or simultaneously with step (c), contacting said test sample with a receptor for said analyte, or with an additional anti-analyte antibody which is directed to a different epitopic site on said analyte than to that which said second antibody, if present, is directed, or than to that which the conjugate antibody is directed, if said conjugate antibody is directed to an epitopic site on said analyte.

12. The method according to claim 11 wherein either said analyte receptor or said additional anti-analyte antibody is immobilized upon a solid phase.

13. The method according to claim 11 wherein said solid phase comprises a paramagnetic particle.

14. The method according to claim 10 wherein said variant RNA replication products are labeled prior to detection or prior to detection and quantitation.

15. The method according to claim 14 wherein said replication products are labeled with a radionuclide, an enzyme, a coenzyme, a fluorescer, a chemiluminescer, a chromogen, an enzyme substrate, an enzyme co-factor, an enzyme inhibitor, a free radical, a particle, or a dye.

16. The method according to claim 14 wherein said replication products are labeled during replication.

17. The method according to claim 10 wherein the detection or detection and quantitation of the RNA replication products comprises labeling said RNA replication products with an acridinium ester.

18. An immunoassay method to detect, or to detect and quantitate, two or more different analytes simultaneously in a test sample, comprising:
performing the method of claim 10 simultaneously with two or more different antibody-variant DNA conjugates, wherein said variant DNA of the conjugates comprises DNA sequences inserted therein, wherein said inserted DNA sequences are the same in variant DNA that is conjugated to antibodies having similar binding specificities, and wherein said inserted DNA sequences are different between conjugates whose antibodies have different binding specificities.

* * * * *

UNITED STATES PATENT AND TRADEMARK OFFICE
CERTIFICATE OF CORRECTION

PATENT NO. : 6,083,689
DATED : July 4, 2000
INVENTOR(S) : Richard A. Martinelli

It is certified that error appears in the above-identified patent and that said Letters Patent are hereby corrected as shown below:

Title page, Section [75] Inventors, "Eddie Carroll, III, Waltham Mass." should be deleted as an inventor.

Column 17, line 33, "the conjugate" should read -- said conjugate --.

Signed and Sealed this

Twenty-fourth Day of April, 2001

Attest:

NICHOLAS P. GODICI

Attesting Officer    Acting Director of the United States Patent and Trademark Office

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 90 base pairs
      (B) TYPE: nucleic acid
      (C) STRANDEDNESS: single
      (D) TOPOLOGY: linear (ii) MOLECULE TYPE: DNA (nanovariant)

(xi) SEQUENCE DESCRIPTION: SEQ ID NO:1:

```
GGGGAAATCC TGTTACCAGG ATAACGGGGT TTTCTCACCT CTCTACTCGA AAGTTAGAGA         60

GGACACACCC GGATCTAGCC GGGTCAACCC                                         90
```